(12) United States Patent
Ikami

(10) Patent No.: US 7,528,398 B2
(45) Date of Patent: May 5, 2009

(54) FLUORESCENCE IMAGING METHOD AND APPARATUS UTILIZING A FIXED EXCITATION SOURCE

(75) Inventor: Seishi Ikami, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1247 days.

(21) Appl. No.: 10/401,029

(22) Filed: Mar. 28, 2003

(65) Prior Publication Data

US 2003/0214581 A1    Nov. 20, 2003

(30) Foreign Application Priority Data

Mar. 28, 2002  (JP) .............................. 2002-092234

(51) Int. Cl.
*G01N 21/64* (2006.01)
*H01J 29/02* (2006.01)

(52) U.S. Cl. .............. 250/522.1; 250/458.1; 250/459.1; 250/461.2; 356/344

(58) Field of Classification Search .............. 250/522.1, 250/458.1, 459.1, 461.1, 461.2; 356/344
See application file for complete search history.

(56) References Cited

U.S. PATENT DOCUMENTS 5,774,214 A * 6/1998 Prettyjohns ................. 356/344
5,856,866 A * 1/1999 Shimizu et al. ............... 356/73
6,458,410 B1 * 10/2002 Ikami et al. ................. 427/2.11

FOREIGN PATENT DOCUMENTS

| JP | 55-133437 | 3/1979 |
|---|---|---|
| JP | 7-99604 A | 4/1995 |
| JP | 2000-180922 A | 6/2000 |
| WO | WO 01/63247 A2 | 8/2001 |

* cited by examiner

*Primary Examiner*—David P Porta
*Assistant Examiner*—Jessica L Eley
(74) *Attorney, Agent, or Firm*—Sughrue Mion, PLLC

(57) ABSTRACT

An imaging section is secured to a casing, and an object is supported on an object support section, which is located within the casing. The object support section is moved within the casing in order for an imaging distance between the imaging section and the object, which has been supported on the object support section, to be altered. Excitation light is irradiated to the object, which has been supported on the object support section, with an excitation light source, which is secured to the object support section. A distribution of illuminances of the excitation light on the object is thus prevented from fluctuating to a fluctuation of the imaging distance.

20 Claims, 6 Drawing Sheets

FLUORESCENCE IMAGING METHOD AND APPARATUS UTILIZING A FIXED EXCITATION SOURCE

BACKGROUND OF THE INVENTION

1. Field of the Invention

This invention relates to an imaging method and apparatus for forming an image of an object supported in a casing. This invention also relates to an image processing method and apparatus for the imaging method and an imaging system comprising the imaging apparatus.

2. Description of the Related Art

Imaging apparatuses, in which an object is supported in a casing, light having been produced by a light source located within the casing is irradiated to the object, and an image of the object is thus formed, have heretofore been used in various fields. For example, in fields of biochemistry, fluorescence detecting systems utilizing a fluorescent substance as a labeling substance have heretofore been known. With the fluorescence detecting systems, analyses of gene sequences and gene expression levels, separation and identification of proteins, and evaluation of molecular weights and characteristics are capable of being performed in accordance with information obtained by reading out fluorescence images.

Specifically, for example, after a fluoro chrome has been added to a liquid containing a plurality of DNA fragments to be subjected to electrophoresis, electrophoresis of the plurality of the DNA fragments may be performed on a gel support. Alternatively, electrophoresis of a plurality of DNA fragments may be performed on a gel support containing a fluoro chrome. As another alternative, after electrophoresis of a plurality of DNA fragments has been performed on a gel support, the DNA fragments having been subjected to the electrophoresis may be leveled with a fluoro chrome by, for example, a process for dipping the gel support in a liquid containing the fluoro chrome, the fluoro chrome may then be excited with excitation light to produce fluorescence, the thus produced fluorescence may be detected, and a fluorescence image may thereby be formed. In accordance with the thus formed fluorescence image, a DNA distribution on the gel support is capable of being detected.

As a further alternative, after electrophoresis of a plurality of DNA fragments has been performed on a gel support, the DNA fragments having been subjected to the electrophoresis may be denatured. Thereafter, at least part of the denatured DNA fragments maybe transcribed to a transcription support, such as nitrocellulose, with a Southern blotting technique. The denatured DNA fragments and a probe having been prepared by labeling a DNA or an RNA, which is complementary to a target DNA, with a fluoro chrome, may then be subjected to hybridization. In this manner, only a DNA fragment, which is complementary to the probe DNA or the probe RNA, is selectively labeled with the fluoro chrome. Thereafter, the fluoro chrome, with which the DNA fragment described above has been labeled, may be excited with the excitation light to produce the fluorescence, the thus produced fluorescence may be detected, and a fluorescence image may thereby be formed. In accordance with the thus formed fluorescence image, a target DNA distribution on the transcription support is capable of being detected.

Recently, micro array analysis systems utilizing micro arrays have attracted particular attention as biochemical analysis systems. By way of example, with the micro array analysis systems utilizing a fluorescent substance as a labeling substance, a micro array is prepared by, for example, spotting multiple kinds of specific binding substances, which are capable of specifically binding to organism-originating substances and whose base sequences, base lengths, compositions, and the like, are known, onto different positions on a surface of a carrier, such as a slide glass plate or a membrane filter, by use of a spotting apparatus and thereby forming a plurality of independent spots on the surface of the carrier. Examples of the specific binding substances include hormones, tumor markers, enzymes, antibodies, antigens, abzymes, other proteins, nucleic acids, cDNA's, DNA's, and RNA's. Thereafter, an organism-originating substance, which has been sampled from an organism through extraction, isolation, or the like, or has been subjected to chemical treatment, chemical modification treatment, or the like, and which has been labeled with a fluorescent labeling substance, such as a fluorescent substance or a fluoro chrome, is subjected to hybridization with the specific binding substances, which have been fixed to the spots on the micro array. The organism-originating substance is thus specifically bound to one of the specific binding substances on the micro array. Examples of the organism-originating substances include hormones, tumor markers, enzymes, antibodies, antigens, abzymes, other proteins, nucleic acids, cDNA's, DNA's, and mRNA's. Excitation light is then irradiated to the micro array, and the fluorescence produced by the labeling substance, such as the fluorescent substance or the fluoro chrome, with which the organism-originating substance has been labeled, is photoelectrically detected. In accordance with the results of the photoelectric detection, the organism-originating substance is analyzed.

In the biochemical analysis systems described above, an imaging apparatus comprising an excitation light source and a CCD image sensor, which are located in a casing, is utilized in order to detect the fluorescence, or the like. Also, the micro array described above, a gel, or the like, acting as a sample is accommodated in the casing, and excitation light having been produced by the excitation light source is irradiated to the sample in order to excite the sample to produce the fluorescence. An image of the thus produced fluorescence is formed with the CCD image sensor acting as imaging means.

Besides the imaging apparatuses utilized in the biochemical analysis systems, there have heretofore been known imaging apparatuses, in which an object is accommodated in a casing provided with a light source, light having been produced by the light source is irradiated to the object, and an image of the object is formed with an imaging section. The imaging apparatuses have a structure, such that the position of the light source for producing the light (or excitation light) is fixed at a predetermined position.

However, sizes of the objects whose images are to be formed take various values. Therefore, the conventional imaging apparatuses are constituted such that an object is capable of being located at one of various different height positions in accordance with the size of the object. Specifically, the object is supported by a sample tray having an approximately plate-like shape, the sample tray is held at one of stages of a tray holding section, which stages are located within the casing, and an imaging operation is performed in this state. In this manner, images of objects having different sizes are capable of being formed with the imaging means.

However, in cases where the position of the object is altered, while the position of the light source is being fixed at the predetermined position, the intensity of the light irradiated from the light source to the object, the distribution of illuminances of the light, and the like, vary in accordance with the position at which the object is located. Therefore, the problems occur in that the image quality of the thus formed image is affected adversely. Specifically, in cases where the imaging distance between the object and the light source is altered, the angle of incidence of the excitation light upon the object varies, and the intensity of the excitation light impinging upon the object varies. Therefore, the problems occur in that, in cases where the imaging distance is altered, image information is acquired under different imaging conditions.

Also, in cases where the obtained image information is subjected to a shading correction, the problems occur in that, since the imaging conditions vary for different imaging distances, correcting conditions must be set for each of different object heights.

SUMMARY OF THE INVENTION

The primary object of the present invention is to provide an imaging method, wherein problems are capable of being prevented from occurring in that a distribution of illuminances of excitation light on an object fluctuates due to a fluctuation of an imaging distance, image quality of an obtained image is capable of being prevented from becoming bad, and an efficiency of an image correction is capable of being enhanced.

Another object of the present invention is to provide an imaging apparatus for carrying out the imaging method.

A further object of the present invention is to provide an image processing method for the imaging method.

A still further object of the present invention is to provide an image processing apparatus for carrying out the image processing method.

The specific object of the present invention is to provide an imaging system comprising the imaging apparatus.

The present invention provides an imaging method, in which an object is accommodated within a casing, and an imaging operation for forming an image of the object accommodated within the casing is performed with an imaging section, which is secured to the casing, image information being acquired from the imaging operation, the method comprising the steps of:

i) supporting the object on an object support section, which is located within the casing, ii) moving the object support section within the casing in order for an imaging distance between the imaging section and the object, which has been supported on the object support section, to be altered, and iii) irradiating excitation light to the object, which has been supported on the object support section, with an excitation light source, which is secured to the object support section.

The present invention also provides an imaging apparatus, comprising a casing, in which an object is accommodated, and an imaging section, which is secured to the casing and performs an imaging operation for forming an image of the object accommodated within the casing in order to acquire image information, wherein the improvement comprises the provision of:

i) an object support section, which is located within the casing and on which the object is to be supported, ii) an excitation light source, which is secured to the object support section, the excitation light source irradiating excitation light to the object, which has been supported on the object support section, and iii) an object moving section for moving the object support section within the casing in order to alter an imaging distance between the imaging section and the object, which has been supported on the object support section.

The excitation light source may be an excitation light source, which irradiates the excitation light directly to the object support section within the casing. Alternatively, the excitation light source may be an excitation light irradiating section for irradiating the excitation light, which has been produced by an excitation light producing section located on the side outward from the casing, via an excitation light guiding section.

The present invention further provides an image processing method for correcting image information, which has been acquired from an imaging operation for forming an image of an object, the imaging operation being performed with an imaging section in a state, in which the object is supported on an object support section located for movement within a casing, and in which excitation light is irradiated from an excitation light source to the object, the excitation light source being secured to the object support section, the method comprising the steps of:

i) making an analysis of an imaging region on the object support section, which imaging region has been subjected to the imaging operation performed with the imaging section, the analysis being made by use of an imaging distance between the object and the imaging section, ii) setting correcting conditions with respect to the imaging region, which has been analyzed, in accordance with a distribution of illuminances of the excitation light, which distribution is formed on the object support section by the excitation light source, and iii) correcting the image information, which has been acquired from the imaging section, in accordance with the correcting conditions, which have been set.

The present invention still further provides an image processing apparatus for correcting image information, which has been acquired from an imaging operation for forming an image of an object, the imaging operation being performed with an imaging section in a state, in which the object is supported on an object support section located for movement within a casing, and in which excitation light is irradiated from an excitation light source to the object, the excitation light source being secured to the object support section, the apparatus comprising:

i) region analyzing means for making an analysis of an imaging region on the object support section, which imaging region has been subjected to the imaging operation performed with the imaging section, the analysis being made by use of an imaging distance between the object and the imaging section, ii) correcting condition setting means for setting correcting conditions with respect to the imaging region, which has been analyzed by the region analyzing means, in accordance with a distribution of illuminances of the excitation light, which distribution is formed on the object support section by the excitation light source, and iii) image correcting means for correcting the image information, which has been acquired from the imaging section, in accordance with the correcting conditions, which have been set by the correcting condition setting means.

The correcting conditions may be the conditions, with which noise due to the distribution of illuminances of the excitation light is capable of being eliminated. The correcting conditions may contain parameters for making a compensation for other kinds of noise.

The present invention also provides an imaging system, comprising:

an imaging apparatus provided with a casing, in which an object is accommodated, and an imaging section, which is secured to the casing and performs an imaging operation for forming an image of the object accommodated within the casing in order to acquire image information, and an image processing apparatus for correcting the image information, which has been acquired from the imaging apparatus, wherein the imaging apparatus comprises:
  i) an object support section, which is located within the casing and on which the object is to be supported,
  ii) an excitation light source, which is secured to the object support section, the excitation light source irradiating excitation light to the object, which has been supported on the object support section, and
  iii) an object moving section for moving the object support section within the casing in order to alter an imaging distance between the imaging section and the object, which has been supported on the object support section, and the image processing apparatus comprises:
  a) region analyzing means for making an analysis of an imaging region on the object support section, which imaging region has been subjected to the imaging operation performed with the imaging section, the analysis being made by use of an imaging distance between the object and the imaging section,
  b) correcting condition setting means for setting correcting conditions with respect to the imaging region, which has been analyzed by the region analyzing means, in accordance with a distribution of illuminances of the excitation light, which distribution is formed on the object support section by the excitation light source, and
  c) image correcting means for correcting the image information, which has been acquired from the imaging apparatus, in accordance with the correcting conditions, which have been set by the correcting condition setting means.

The imaging system in accordance with the present invention maybe modified such that the image processing apparatus further comprises movement controlling means for controlling operations of the object moving section.

With the imaging method and apparatus in accordance with the present invention, the excitation light source for irradiating the excitation light to the object, which has been supported on the object support section, is secured to the object support section. Therefore, in cases where the object support section is moved within the casing in order to alter the imaging distance between the imaging section and the object, which has been supported on the object support section, the relationship between the position of the excitation light source and the position of the object does not change. Accordingly, the problems are capable of being prevented from occurring in that the image quality of the obtained image becomes bad due to fluctuation of the intensity of the excitation light impinging upon the object and fluctuation of the distribution of illuminances of the excitation light on the object.

With the image processing method and apparatus and the imaging system in accordance with the present invention, by the utilization of the characteristics, such that the distribution of illuminances of the excitation light, which distribution is formed by the excitation light source secured to the object support section, does not alter due to the movement of the object support section, an analysis is made as to the imaging region on the object support section, which imaging region has been subjected to the imaging operation performed with the imaging section. The analysis is made in accordance with the imaging distance between the object and the imaging section. Also, the correcting conditions with respect to the imaging region, which has been analyzed, are extracted from a correction table, in which the correcting conditions have been set with respect to each of regions of the object support section and in accordance with the distribution of illuminances of the excitation light. Further, the image information, which has been acquired from the imaging section, is corrected in accordance with the thus extracted correcting conditions. Therefore, it is not necessary that correction tables are prepared for different imaging distances. Accordingly, the setting of the correcting conditions is capable of being performed efficiently.

In cases where the image processing apparatus is provided with the movement controlling means, the operation for altering the height of the object is capable of being performed from the side of the image processing apparatus. Therefore, in cases where the height of the object is to be altered, the user need not operate the object, which has been accommodated within the casing, or the object support section located within the casing. Accordingly, the imaging system in accordance with the present invention is easy for the user to use. Also, the problems are capable of being prevented from occurring in that the imaging conditions alter due to an operation for taking the object out of the casing.

DESCRIPTION OF THE PREFERRED EMBODIMENTS

The present invention will hereinbelow be described in further detail with reference to the accompanying drawings.

Figure 1:
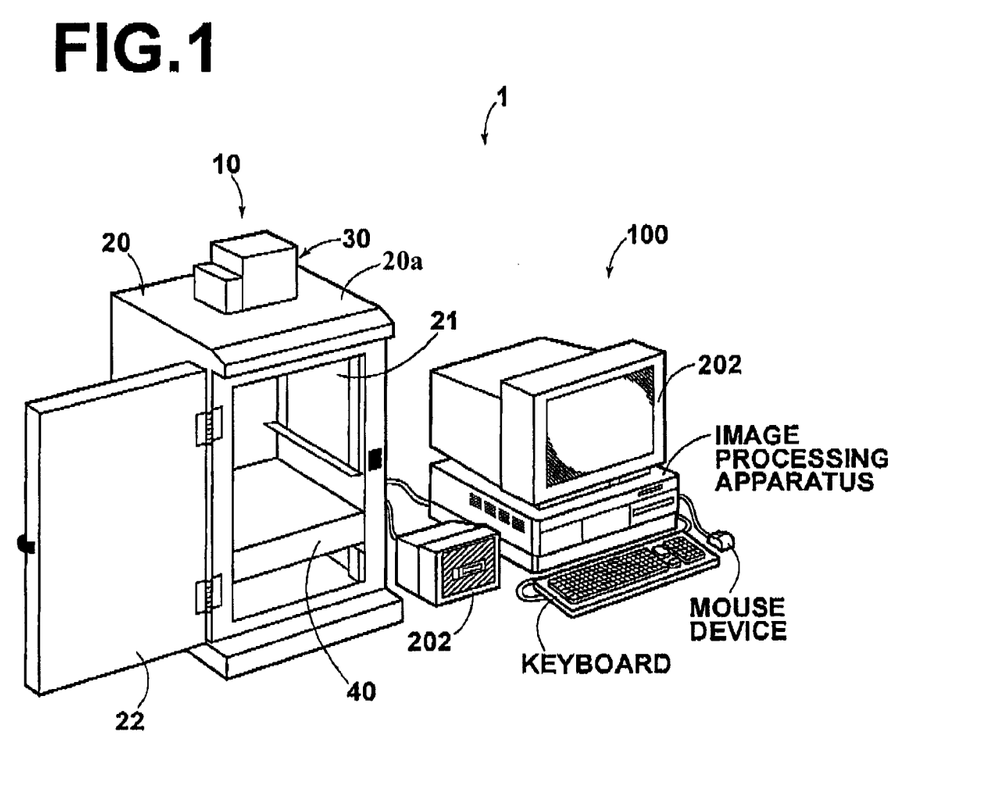
FIG. 1 is a perspective view showing an embodiment of the imaging system in accordance with the present invention.

FIG. 1 is a perspective view showing an embodiment of the imaging system in accordance with the present invention. An imaging system 1 will be described hereinbelow with reference to FIG. 1. By way of example, the imaging system 1 is constituted as a fluorescence detecting system for irradiating excitation light to a fluorescent substance, which acts as an object, and displaying an acquired fluorescence image. The imaging system 1 comprises an imaging apparatus 10 and an image processing apparatus 100. The imaging apparatus 10 and the image processing apparatus 100 are of the types located on a desk. The image processing apparatus 100 is constituted of, for example, a computer. The imaging apparatus 10 performs an imaging operation for forming an image of an object PS and feeds image information IG of the object PS, which image information has been obtained from the imaging operation, into the image processing apparatus 100.

The image processing apparatus 100 performs image processing on the image information IG. A visible image is reproduced from the processed image information IG and is displayed on a display section 202.

Figure 2:
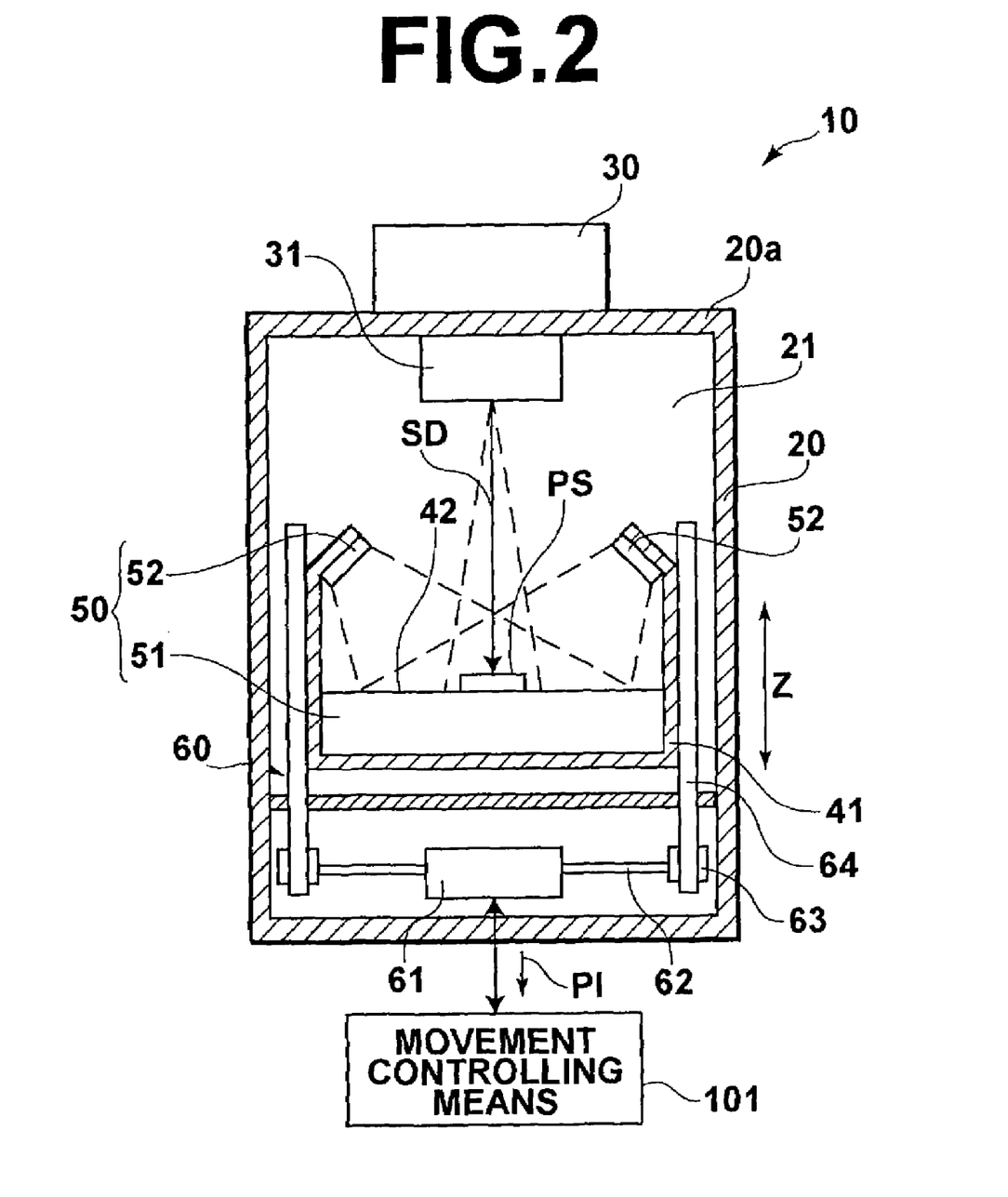
FIG. 2 is a side sectional view showing a first embodiment of the imaging apparatus in accordance with the present invention.

FIG. 2 is a side sectional view showing a first embodiment of the imaging apparatus in accordance with the present invention. The imaging apparatus 10 will be described hereinbelow with reference to FIG. 1 and FIG. 2. The imaging apparatus 10 comprises a casing 20, an imaging section 30, an object support section 40, an excitation light source 50, an object moving section 60, and the like. As illustrated in FIG. 1, the casing 20 has an approximately rectangular parallelepiped shape and has a hollow region 21 within the casing 20. Also, the casing 20 is provided with an openable cover 22. Therefore, the user is capable of opening the cover 22 and accommodates the object PS within the casing 20. In this manner, the casing 20 is constituted as a dark box such that external light does not enter into the hollow region 21.

The imaging section 30 is secured to a top surface 20a of the casing 20. The imaging section 30 performs the imaging operation for forming an image of the object PS, which has been located within the casing 20. By way of example, the imaging section 30 is constituted of a CCD camera, or the like. The imaging section 30 is provided with a cooling section (not shown). The imaging section 30 is cooled by the cooling section, and the problems are thus prevented from occurring in that noise components due to dark current are contained in the image information obtained from the CCD camera. A lens section 31 is fitted to the imaging section 30. The lens section 31 is capable of being moved in the direction indicated by the double headed arrow Z. The lens section 31 is thus moved in the direction indicated by the double headed arrow Z, and the focus is thereby adjusted at the position of the object PS.

The object support section 40 has a support surface 42, on which the object PS is located and supported. The object support section 40 is located within the hollow region 21 of the casing 20. The object support section 40 comprises a housing 41 and the support surface 42. The object support section 40 has a structure, such that the object PS is capable of being located on the support surface 42, which is located within the housing 41. Also, the object support section 40 is supported by the object moving section 60. The object support section 40 is capable of being moved in the direction indicated by the double headed arrow Z by the actuation of the object moving section 60.

The excitation light source 50, which may be constituted of, for example, LED's, is secured to the object support section 40. The excitation light source 50 irradiates the excitation light, which excites the fluorescent substance acting as the object PS to produce the fluorescence, to the object PS. The excitation light source 50 comprises a bottom excitation light source 51 and downward irradiating excitation light sources 52, 52. The bottom excitation light source 51 is located on the side downward from the support surface 42 of the housing 41. The downward irradiating excitation light sources 52, 52 are located on the side upward from the support surface 42 of the housing 41. Therefore, the bottom excitation light source 51 irradiates the excitation light from below the object PS. The downward irradiating excitation light sources 52, 52 irradiate the excitation light from above the object PS. Particularly, the downward irradiating excitation light sources 52, 52 are located at the positions such that the distribution of illuminances of the excitation light and the distribution of intensities of the excitation light, which distributions are formed on the support surface 42, become optimum, i.e. such that the distributions described above become closest to uniform distributions.

The object moving section 60 moves the object support section 40 in the direction indicated by the double headed arrow Z. The object moving section 60 comprises a driving section 61, which may be constituted of a motor, or the like. The object moving section 60 also comprises a shaft 62, which is connected to the driving section 61. The object moving section 60 further comprises pulleys 63, 63, which are secured to the shaft 62. The object moving section 60 still further comprises belts 64, 64, each of which is threaded over one of the pulleys 63, 63 and is moved in the direction indicated by the double headed arrow Z by the rotation of the pulley 63. The object support section 40 is secured to the belts 64, 64. When the driving section 61 is actuated, the object support section 40 is moved in the direction indicated by the double headed arrow Z by the operations of the shaft 62, the pulleys 63, 63, and the belts 64, 64. The operation of the object moving section 60 is controlled by a movement controlling means 101. Also, the object moving section 60 is provided with, for example, an encoder. The object moving section 60 detects object position information PI from the movement distance of the object support section 40 and feeds the object position information PI into the movement controlling means 101. Specifically, the driving section 61 of the object moving section 60 acts also as an object position detecting section.

As illustrated in FIG. 2, the excitation light source 50 is secured to the object support section 40. Therefore, in cases where the object support section 40 is moved, and an imaging distance SD is thus altered, the relationship between the position of the object support section 40 and the position of the excitation light source 50 does not change. Specifically, the intensity of the excitation light impinging upon the support surface 42 does not depend upon the imaging distance SD and is kept approximately at a predetermined value. Also, the distribution of illuminances of the excitation light, which distribution is formed on the support surface 42, does not depend upon the imaging distance SD and is kept approximately at a predetermined distribution. Therefore, it is not necessary that correcting conditions RC are set in accordance with the imaging distance SD. Accordingly, an image correction is capable of being performed efficiently. Also, the image quality of the obtained image is capable of being enhanced.

In order for the imaging distance SD to be altered, it may be considered that the imaging section 30 is moved or that the object PS is moved. However, since the imaging section 30 should be cooled, the imaging section 30 should preferably be located on the side outward from the casing 20. Therefore, in this embodiment, the object support section 40 is moved in order for the imaging distance SD to be altered.

Figure 3:
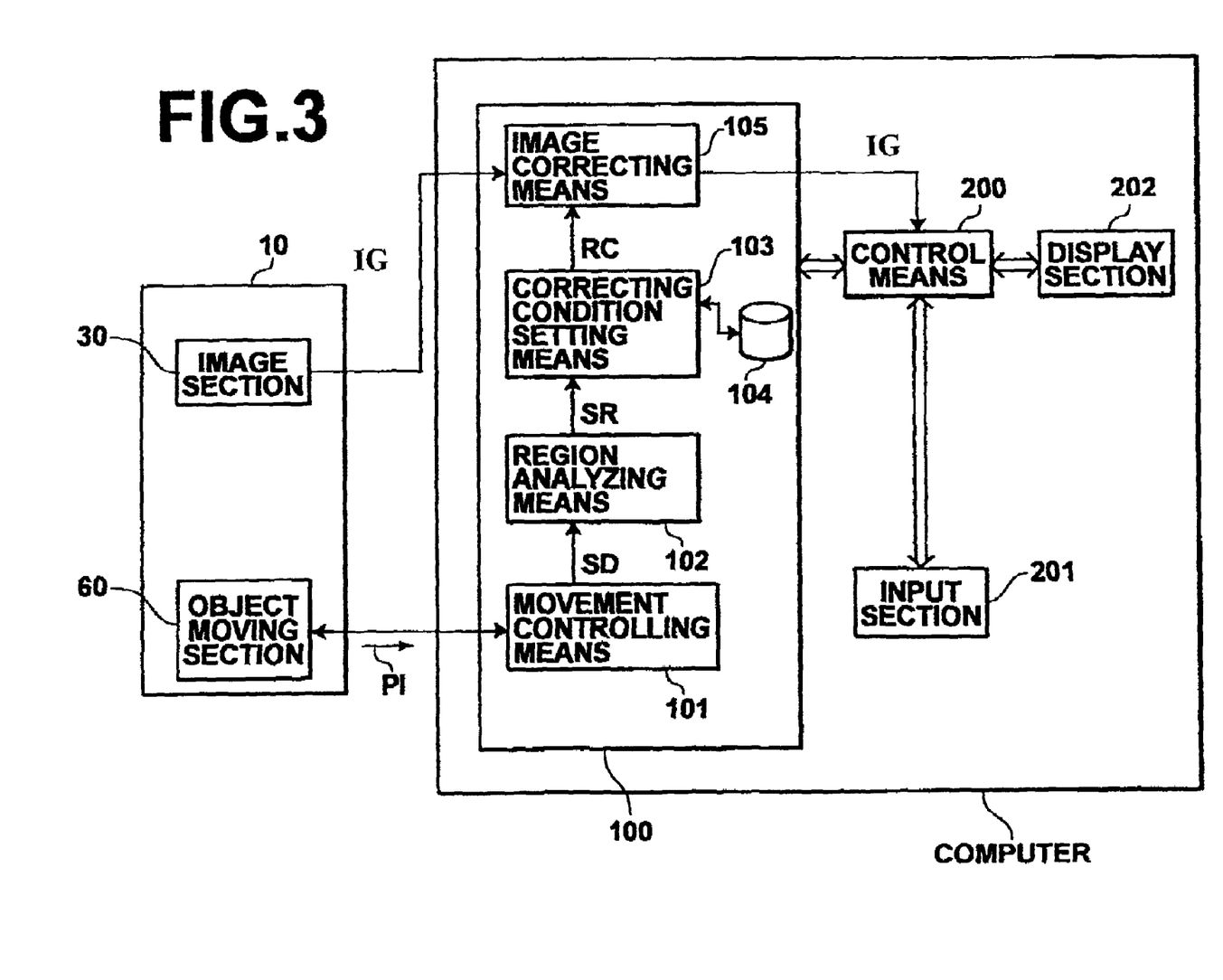
FIG. 3 is a block diagram showing an embodiment of the image processing apparatus in accordance with the present invention.

FIG. 3 is a block diagram showing an embodiment of the image processing apparatus in accordance with the present invention. The image processing apparatus 100 will be described hereinbelow with reference to FIG. 3. The image processing apparatus 100 is connected to the imaging apparatus 10. The image processing apparatus 100 receives the image information IG from the imaging apparatus 10 and performs the image processing on the image information IG. A visible image is reproduced from the processed image information IG and is displayed on the display section 202. The image processing apparatus 100 has the functions for performing various kinds of image processing on the obtained image information. In this embodiment, the functions of the image processing apparatus 100 for making shading compensation will be described later. Also, the image processing apparatus 100 is provided with means for controlling the operation of the imaging section 30 of the imaging apparatus 10 and the operation of the excitation light source 50 of the imaging apparatus 10. The image processing apparatus 100 may thus have the functions for controlling the exposure of the imaging section 30 to the fluorescence and the on-off operation of the excitation light source 50.

As illustrated in FIG. 3, the image processing apparatus 100 comprises the movement controlling means 101, region analyzing means 102, correcting condition setting means 103, and image correcting means 105. The movement controlling means 101 has the functions for controlling the operation of the object moving section 60 and obtaining the object position information PI of the object PS from the extent of operation of the driving section 61 of the object moving section 60. Specifically, the movement controlling means 101 stores the position information representing the position of the imaging section 30 secured to the casing 20. The movement controlling means 101 calculates the imaging distance SD in accordance with the position information representing the position of the imaging section 30 and the object position information PI of the object PS supported on the object support section 40. The movement controlling means 101 makes a judgment as to the imaging distance SD in accordance with the object position information PI and feeds information, which represents the results of the judgment, into the region analyzing means 102.

Also, the user is capable of operating an input section 201 and thereby operating the object moving section 60 via control means 200 and the movement controlling means 101. The object position information PI of the object PS is fed through the control means 200 into the display section 202 and is displayed on the display section 202. The user is capable of adjusting the imaging distance SD by operating the input section 201 in accordance with the object position information PI displayed on the display section 202.

As described above, the movement controlling means 101 is located within the image processing apparatus 100. Therefore, in cases where the imaging distance SD is to be adjusted, it is not necessary that the cover 22 of the casing 20 is opened. Therefore, the problems are capable of being prevented from occurring in that the imaging conditions change due to the opening of the cover 22. Also, in cases where the user adjusts the imaging distance SD, it is not necessary that the user moves from the position for operating the computer to the side of the imaging apparatus 10 in order to adjust the height of the object PS. Therefore, after the object PS has been located on the object support section 40, the setting of the fine imaging conditions is capable of being performed only on the side of the image processing apparatus 100.

The region analyzing means 102 has the functions for making an analysis as to an imaging region SR of the image information IG by use of the information representing the imaging distance SD, which information is received from the movement controlling means 110. Also, the region analyzing means 102 feeds information, which represents the analyzed imaging region SR, into the correcting condition setting means 103. Specifically, the imaging region SR on the object support section 40, which imaging region is represented by the image information IG having been obtained from the imaging section 30, is in proportion to the imaging distance SD. Specifically, in cases where the imaging distance SD becomes long, the imaging region SR becomes large. In cases where the imaging distance SD becomes short, the imaging region SR becomes small. Therefore, the region analyzing means 102 is capable of analyzing the imaging region SR in accordance with the imaging distance SD. It often occurs that the imaging region SR alters due to, for example, an operation of a focusing servo of the lens section 31. Therefore, the region analyzing means 102 may analyze the imaging region SR with the operation of the lens section 31 being taken into consideration.

The correcting condition setting means 103 sets the correcting conditions RC to be used for the shading compensation performed on the image information IG obtained from the imaging section 30. The correcting condition setting means 103 is capable of accessing a correction table 104. The correction table 104 stores information representing the correcting conditions RC with respect to each of regions constituting the entire imaging region of the object support section 40. The correcting conditions RC have been formed in the manner described below. Specifically, a reference image having uniform image density distribution on the object support section 40 is read out by the imaging section 30, and conversion characteristics are calculated with respect to the entire region of the reference image. Also, the correcting conditions RC are formed in accordance with the calculated conversion characteristics.

The correction table 104 has been formed by the utilization of the characteristics such that the relationship between the position of the object PS and the position of the excitation light source 50 is kept approximately at a predetermined relationship. Specifically, since the excitation light source 50 is secured to the object support section 40, the distribution of illuminances of the excitation light, which distribution is formed on the object support section 40, is kept approximately at a predetermined distribution regardless of the position of the object support section 40. Therefore, the correcting conditions RC with respect to each of the regions constituting the entire imaging region of the object support section 40 may be calculated previously in accordance with the distribution of intensities of the excitation light and the distribution of illuminances of the excitation light, which distributions are formed on the object support section 40. In such cases, the thus calculated correcting conditions RC are capable of being used regardless of the value of the imaging distance SD.

The correcting condition setting means 103 extracts the correcting conditions RC, which correspond to the imaging region SR having been analyzed by the region analyzing means 102, from the correction table 104 and sets the correcting conditions RC with respect to each of pixels of the imaging section 30. The correcting condition setting means 103 feeds information, which represents the thus set correcting conditions RC, into the image correcting means 105.

In this embodiment, as described above, the correcting condition setting means 103 extracts the correcting conditions RC for the image information in accordance with the correction table 104, in which the correcting conditions RC have been set previously. Alternatively, the correction table 104 may store only the information representing the distribution of illuminances of the excitation light, which distribution is formed on the object support section 40, and the correcting condition setting means 103 may calculate the correcting conditions RC for the image information in accordance with the distribution of illuminances of the excitation light.

The image correcting means 105 performs the shading compensation on the image information IG, which is received from the imaging section 30, by use of the correcting conditions RC, which are received from the correcting condition setting means 103. Specifically, image correcting means 105 performs the image correction with respect to each of the regions, which are represented by the image information IG, by use of the correcting conditions RC, which correspond to each of the regions represented by the image information IG.

Also, the image correcting means 105 feeds the thus corrected image information IG into the control means 200. The corrected image information IG is fed from the control means 200 into the display section 202.

Figure 4:
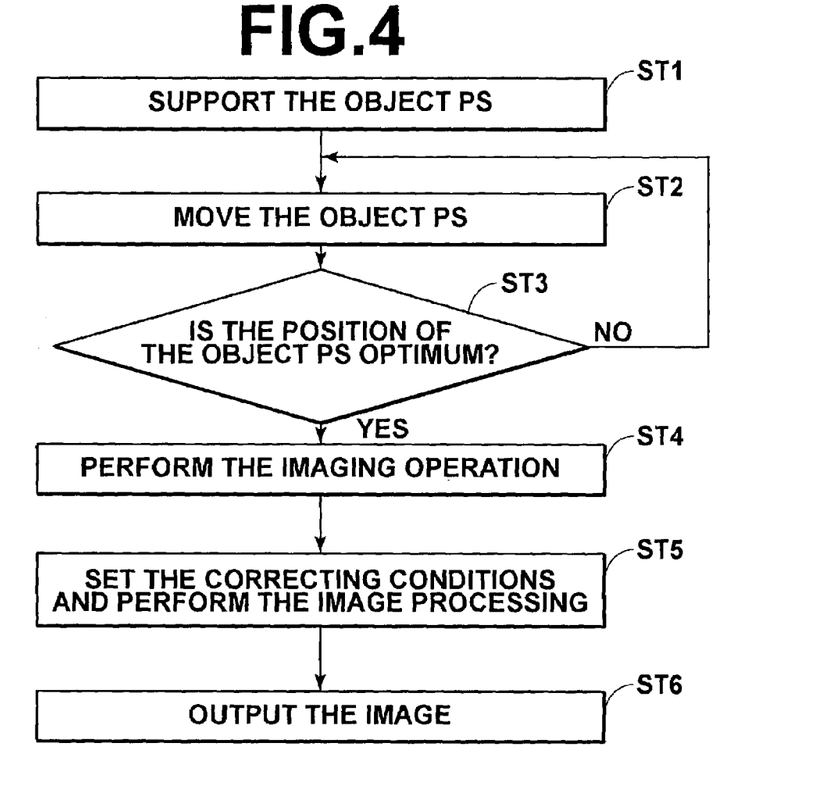
FIG. 4 is a flow chart showing how the embodiment of the imaging system in accordance with the present invention operates.

FIG. 4 is a flow chart showing how the imaging system 1 operates. How the imaging system 1 operates will be described hereinbelow with reference to FIG. 1, FIG. 2, FIG. 3, and FIG. 4. Firstly, in a step ST1, the user opens the cover 22 of the casing 20 shown in FIG. 1 and locates the object PS on the object support section 40. The user then closes the cover 22 such that external light does not enter into the casing 20.

Thereafter, in a step ST2, the user operates the object moving section 60 from the side of the image processing apparatus 100 in order to adjust the imaging distance SD. At this time, the user sees an object preview screen on the display section 202, and operates the object moving section 60. In the step ST2 and a step ST3, the operation is performed until the imaging distance SD of the object PS becomes optimum. In cases where the object PS is moved, when necessary, the focusing servo operation of the lens section 31 is performed. In cases where the object moving section 60 is operated, the object position information PI is fed from the object moving section 60 into the movement controlling means 101.

After the position of the object PS has been adjusted, the setting of the imaging conditions, such as the exposure time, is performed from the side of the computer. Thereafter, in a step ST4, the imaging operation for forming the image of the object PS is performed with the imaging section 30 and under the imaging conditions, which have been set by the user. Also, the image information IG having been obtained from the imaging operation is fed from the imaging section 30 into the image correcting means 105. Thereafter, in a step ST5, image processing, such as the shading compensation processing, is performed on the image information IG by the image correcting means 105. In a step ST6, the image information IG having thus been processed is fed from the image correcting means 105 into the display section 202.

Figure 5:
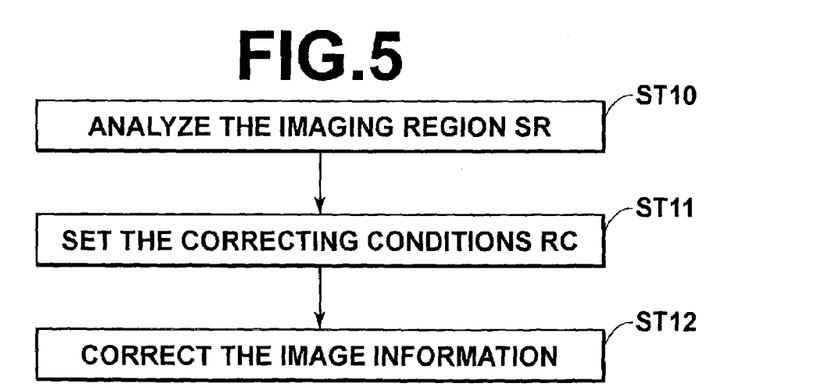
FIG. 5 is a flow chart showing how the embodiment of the image processing apparatus in accordance with the present invention operates.

FIG. 5 is a flow chart showing how the image correction is performed in the imaging system 1. How the image correction is performed will be described hereinbelow with reference to FIG. 1, FIG. 2, FIG. 3, FIG. 4, and FIG. 5. Firstly, when the position of the object support section 40 has been adjusted at the predetermined position by the object moving section 60 in the manner described above, the object position information PI is fed from the object moving section 60 into the movement controlling means 101. In the movement controlling means 101, the imaging distance SD between the object PS and the imaging section 30 is detected. The information representing the imaging distance SD is fed from the movement controlling means 101 into the region analyzing means 102.

Thereafter, as illustrated in FIG. 5, in a step ST10, the region analyzing means 102 analyzes the imaging region SR, which is represented by the image information IG having been acquired from the imaging section 30, in accordance with the imaging distance SD. The information representing the analyzed imaging region SR is fed from the region analyzing means 102 into the correcting condition setting means 103.

Thereafter, in a step ST11, the correcting condition setting means 103 extracts the correcting conditions RC, which are to be used for the correction of the image information IG, from the correction table 104 and in accordance with the received information representing the imaging region SR. The information representing the extracted correcting conditions RC is fed from the correcting condition setting means 103 into the image correcting means 105. In a step ST12, the shading compensation processing is performed on the image information IG by the image correcting means 105. Thereafter, the processed image information IG is fed from the image correcting means 105 into the control means 200 and then into the display section 202. The display section 202 reproduces a visible image from the processed image information IG and displays the visible image.

As described above, the excitation light source 50 is secured to the object support section 40 and is moved together with the object support section 40. Therefore, the characteristics are obtained, such that the distribution of intensities of the excitation light and the distribution of illuminances of the excitation light, which distributions are formed on the object support section 40, become approximately identical with predetermined distributions. By the utilization of the characteristics described above, the correcting conditions RC with respect to each of regions constituting the entire imaging region of the object support section 40, which image region is formed by the excitation light source 50, are set previously in the correction table 104. In such cases, by use of the correction table 104, various pieces of image information IG, which are acquired from imaging operations performed at various lengths of the imaging distance SD, are capable of being corrected. Therefore, it is not necessary that the correcting conditions are set for each of various lengths of the imaging distance SD. Accordingly, the efficiency with which the operation for setting the correcting conditions is capable of being enhanced, and the efficiency of the correction processing is capable of being kept high.

Figure 6:
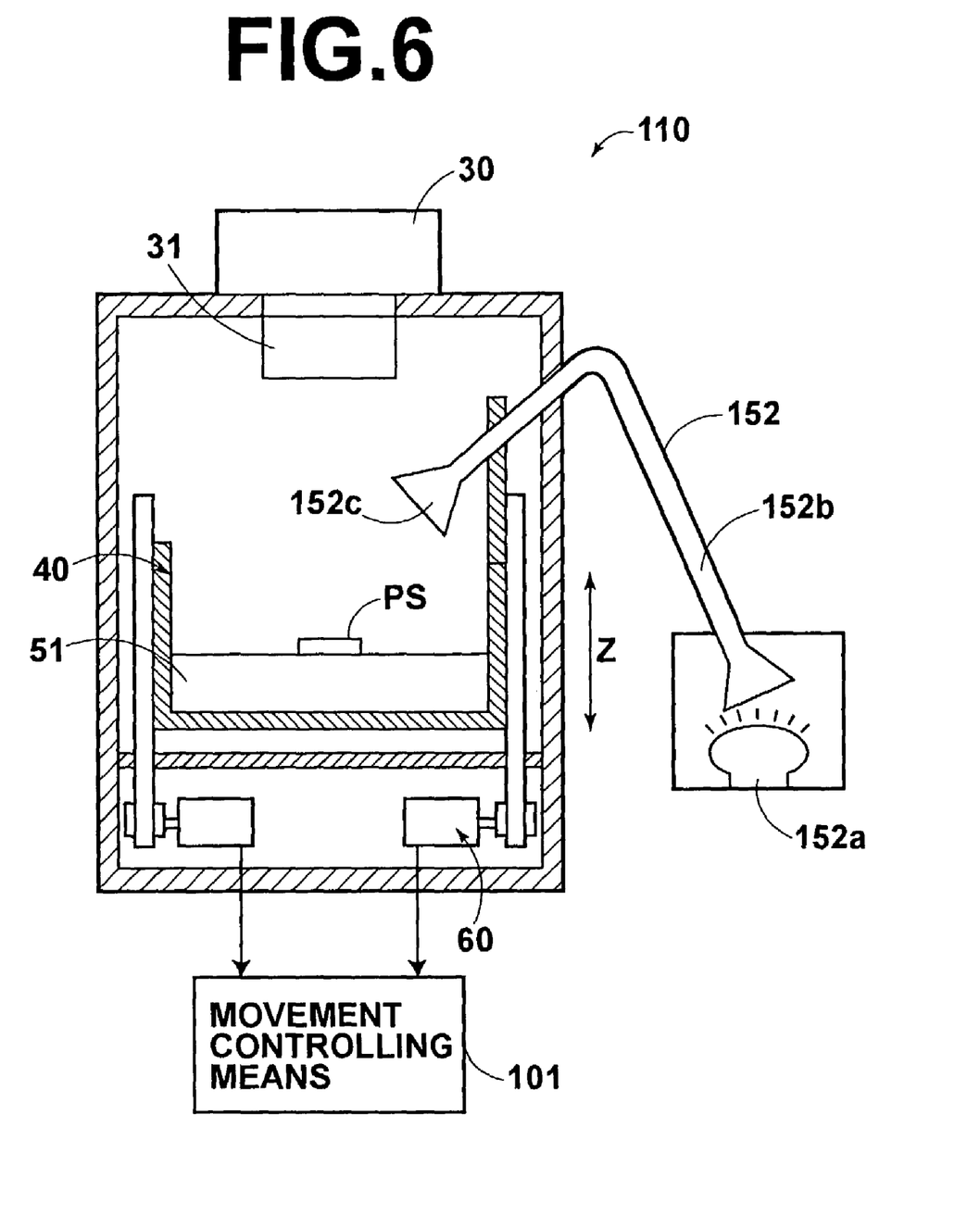
FIG. 6 is a side sectional view showing a second embodiment of the imaging apparatus in accordance with the present invention.

FIG. 6 is a side sectional view showing a second embodiment of the imaging apparatus in accordance with the present invention. An imaging apparatus 110, which is the second embodiment of the imaging apparatus in accordance with the present invention, will be described hereinbelow with reference to FIG. 6. In FIG. 6, similar elements are numbered with the same reference numerals with respect to FIG. 2. The imaging apparatus 110 of FIG. 6 is constituted basically in the same manner at that for the imaging apparatus 10 of FIG. 2, except for the structure of the excitation light source. As illustrated in FIG. 6, in this embodiment, an excitation light source comprises the bottom excitation light source 51 and a downward irradiating excitation light source 152. The downward irradiating excitation light source 152 comprises an excitation light producing section 152a, an excitation light guiding section 152b, and an excitation light irradiating section 152c.

The excitation light producing section 152a is located on the side outward from the casing 20. The excitation light producing section 152a may be constituted of, for example, a halogen lamp for producing the excitation light. The excitation light guiding section 152b may be constituted of, for example, optical fibers. The excitation light guiding section 152b guides the excitation light, which has been produced by the excitation light producing section 152a, into the region within the casing 20. The excitation light irradiating section 152c irradiates the excitation light, which has been guided by the excitation light guiding section 152b, to the region within the casing 20. The excitation light irradiating section 152c is secured to the object support section 40 and is moved together with the object support section 40. In cases where the excitation light producing section 152a of the downward irradiating excitation light source 152 is thus located on the side outward from the casing 20, the problems do not occur in that heat generated by the excitation light producing section 152a adversely affect the imaging operation.

Figure 7:
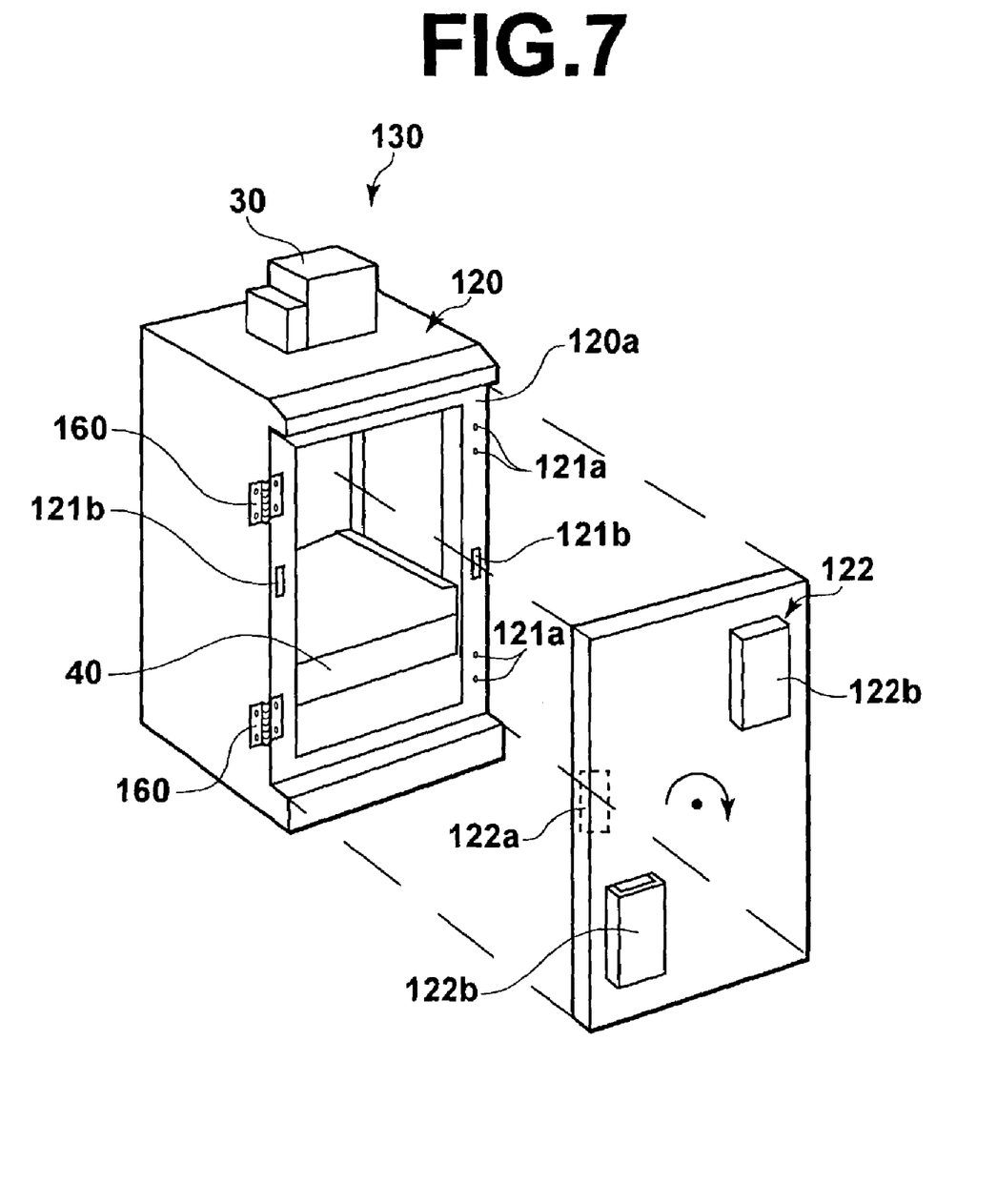
FIG. 7 is a perspective view showing a third embodiment of the imaging apparatus in accordance with the present invention.

FIG. 7 is a perspective view showing a third embodiment of the imaging apparatus in accordance with the present invention. An imaging apparatus 130, which is the third embodiment of the imaging apparatus in accordance with the present invention, will be described hereinbelow with reference to FIG. 7. The imaging apparatus 130 illustrated in FIG. 7 is constituted basically in the same manner as that for the imaging apparatus 10 illustrated in FIG. 2, except for the structure of the casing. In FIG. 7, similar elements are numbered with the same reference numerals with respect to FIG. 2.

The imaging apparatus 130 illustrated in FIG. 7 comprises a casing 120 having a frame 120a. The frame 120a has two upper holes 121a, 121a, which are located on the left-hand side in FIG. 7 for fitting an upper hinge 160, and two lower holes 121a, 121a, which are located on the left-hand side in FIG. 7 for fitting a lower hinge 160. Also, the frame 120a has two upper holes 121a, 121a, which are located on the right-hand side in FIG. 7 for fitting an upper hinge 160, and two lower holes 121a, 121a, which are located on the right-hand side in FIG. 7 for fitting a lower hinge 160. The two upper holes 121a, 121a on the left-hand side are located at positions symmetric with the two upper holes 121a, 121a on the right-hand side. Also, the two lower holes 121a, 121a on the left-hand side are located at positions symmetric with the two lower holes 121a, 121a on the right-hand side. Further, the frame 120a has a left-hand groove 121b for engaging with an engagement section 122a of a cover 122 and a right-hand groove 121b, which is capable of engaging with the engagement section 122a of the cover 122 when the cover 122 is rotated by a degree of 180° as will be described later. The left-hand groove 121b and the right-hand groove 121b are located at positions symmetric with each other. Furthermore, pockets 122b, 122b are formed on the surface of the cover 122. Therefore, the cover 122 is capable of being fitted to either side of the frame 120a. Accordingly, in cases where the imaging apparatus 130 is to be located at a position, at which the cover 122 cannot be opened on the right-hand side, the cover 122 is capable of being rotated by a degree of 180° and fitted to the frame 120a in this orientation, such that the cover 122 is capable of being opened on the left-hand side. In this manner, the flexibility of location of the imaging apparatus 130 is capable of being enhanced, and the imaging apparatus 130 is capable of being used easily.

The aforesaid embodiments may be modified in various other ways. For example, in the embodiments described above, the object PS is supported directly on the object support section 40. Alternatively, the object PS maybe located on a tray capable of transmitting light and may be supported on the object support section 40 via the tray. In such cases, the imaging distance SD alters by the thickness of the tray, and therefore the movement controlling means 101 feeds the object position information PI, which has been obtained with the tray thickness being taken into consideration, into the correcting condition setting means 103.

Also, as illustrated in FIG. 3, the movement controlling means 101 detects the position of the object PS in accordance with the object position information PI received from the object moving section 60. Alternatively, a position detecting section may be located in the casing 20 in order to detects the position of the object support section 40 or the position of the object PS directly and to detect the object position information PI.

Further, the image processing apparatus 100 shown in FIG. 3 operates through the functions of the computer. Alternatively, an image processing program may be set in a computer and utilized for the image processing in co-operation with the computer. Accordingly, the present invention further provides an image processing program for causing a computer to execute an image processing method for correcting image information, which has been acquired from an imaging operation for forming an image of an object, the imaging operation being performed with an imaging section in a state, in which the object is supported on an object support section located for movement within a casing, and in which excitation light is irradiated from an excitation light source to the object, the excitation light source being secured to the object support section, the program comprising the procedures for:

i) making an analysis of an imaging region on the object support section, which imaging region has been subjected to the imaging operation performed with the imaging section, the analysis being made by use of a correction table, in which correcting conditions have been set with respect to each of regions on the object support section in accordance with a distribution of illuminances of the excitation light, the distribution being formed on the object support section by the excitation light source, and by use of an imaging distance between the object and the imaging section, ii) extracting the correcting conditions with respect to the imaging region, which has been analyzed, from the correction table, and iii) correcting the image information, which has been acquired from the imaging section, in accordance with the correcting conditions, which have thus been extracted.

What is claimed is:

1. An imaging method, in which an object is accommodated within a casing, and an imaging operation for forming an image of the object accommodated within the casing is performed with an imaging section, which is secured to the casing, image information being acquired from the imaging operation, the method comprising the steps of:
   i) supporting the object on an object support section, which is located within the casing,
   ii) moving the object support section within the casing in order for an imaging distance between the imaging section and the object, which has been supported on the object support section, to be altered, and
   iii) irradiating excitation light to the object, which has been supported on the object support section, with an excitation light source, which is secured to the object support section.

2. An imaging method, as defined in claim 1 wherein the moving the object support section is in a vertical direction only.

3. An imaging method, as defined in claim 1 wherein the irradiating excitation light to the object comprises a plurality of excitation light sources, which are secured to the object support section, and which irradiate the object from a plurality of directions.

4. An imaging method as defined in claim 1 wherein the excitation light source comprises a downward irradiating excitation light source.

5. An imaging apparatus, comprising a casing, in which an object is accommodated, and an imaging section, which is secured to the casing and performs an imaging operation for forming an image of the object accommodated within the casing in order to acquire image information,
   wherein the improvement comprises the provision of:
   i) an object support section, which is located within the casing and on which the object is to be supported,
   ii) an excitation light source, which is secured to the object support section, the excitation light source irradiating excitation light to the object, which has been supported on the object support section, and
   iii) an object moving section for moving the object support section within the casing in order to alter an imaging distance between the imaging section and the object, which has been supported on the object support section.

6. An imaging apparatus as defined in claim 5 wherein the casing is a dark box, which blocks out external light.

7. An imaging apparatus as defined in claim 5 wherein the excitation light source comprises a downward irradiating excitation light source, which is secured to an upper side of the object support section, and the downward irradiating excitation light source is provided with an excitation light producing section, which produces the excitation light and is located on the side outward from the casing, and an excitation light guiding section for guiding the excitation light, which has been produced by the excitation light producing section, to the region within the casing.

8. An imaging apparatus as defined in claim 5 wherein the object moving section comprises a motor, a shaft connected to the motor, pulleys secured to the shaft, and pulley belts, each of which is threaded over one of the pulleys and is secured to the object support section.

9. An imaging apparatus as defined in claim 5 wherein the excitation light source comprises a downward irradiating excitation light source, which is secured to an upper side of the object support section, and the downward irradiating excitation light source is provided with an excitation light producing section, which produces the excitation light, and an excitation light guiding section for guiding the excitation light, which has been produced by the excitation light producing section, to the region within the casing.

10. An image processing method for correcting image information, which has been acquired from an imaging operation for forming an image of an object, the imaging operation being performed with an imaging section in a state, in which the object is supported on an object support section located for movement within a casing, and in which excitation light is irradiated from an excitation light source to the object, the excitation light source being secured to the object support section, the method comprising the steps of:

i) making an analysis of an imaging region on the object support section, which imaging region has been subjected to the imaging operation performed with the imaging section, the analysis being made by use of an imaging distance between the object and the imaging section, ii) setting correcting conditions with respect to the imaging region, which has been analyzed, in accordance with a distribution of illuminances of the excitation light, which distribution is formed on the object support section by the excitation light source, and iii) correcting the image information, which has been acquired from the imaging section, in accordance with the correcting conditions, which have been set.

11. An image processing apparatus for correcting image information, which has been acquired from an imaging operation for forming an image of an object, the imaging operation being performed with an imaging section in a state, in which the object is supported on an object support section located for movement within a casing, and in which excitation light is irradiated from an excitation light source to the object, the excitation light source being secured to the object support section, the apparatus comprising:

i) region analyzing means for making an analysis of an imaging region on the object support section, which imaging region has been subjected to the imaging operation performed with the imaging section, the analysis being made by use of an imaging distance between the object and the imaging section, ii) correcting condition setting means for setting correcting conditions with respect to the imaging region, which has been analyzed by the region analyzing means, in accordance with a distribution of illuminances of the excitation light, which distribution is formed on the object support section by the excitation light source, and iii) image correcting means for correcting the image information, which has been acquired from the imaging section, in accordance with the correcting conditions, which have been set by the correcting condition setting means.

12. An image processing apparatus as defined in claim 11 wherein the correcting condition setting means is capable of accessing a correction table, the correction table storing information representing the correcting conditions, which have been set previously with respect to each of regions of the object support section in accordance with the distribution of illuminances of the excitation light, which distribution is formed on the object support section by the excitation light source, and the correcting condition setting means extracts the correcting conditions with respect to the imaging region from the correction table and sets the thus extracted correcting conditions.

13. An imaging system, comprising:

an imaging apparatus provided with a casing, in which an object is accommodated, and an imaging section, which is secured to the casing and performs an imaging operation for forming an image of the object accommodated within the casing in order to acquire image information, and an image processing apparatus for correcting the image information, which has been acquired from the imaging apparatus, wherein the imaging apparatus comprises:

i) an object support section, which is located within the casing and on which the object is to be supported, ii) an excitation light source, which is secured to the object support section, the excitation light source irradiating excitation light to the object, which has been supported on the object support section, and iii) an object moving section for moving the object support section within the casing in order to alter an imaging distance between the imaging section and the object, which has been supported on the object support section, and the image processing apparatus comprises:

a) region analyzing means for making an analysis of an imaging region on the object support section, which imaging region has been subjected to the imaging operation performed with the imaging section, the analysis being made by use of an imaging distance between the object and the imaging section, b) correcting condition setting means for setting correcting conditions with respect to the imaging region, which has been analyzed by the region analyzing means, in accordance with a distribution of illuminances of the excitation light, which distribution is formed on the object support section by the excitation light source, and c) image correcting means for correcting the image information, which has been acquired from the imaging apparatus, in accordance with the correcting conditions, which have been set by the correcting condition setting means.

14. An imaging system as defined in claim 13 wherein the casing is a dark box, which blocks out external light.

15. An imaging system as defined in claim 14, wherein the casing includes a door which is configurable for opening from a left-hand side and a right-hand side.

16. An imaging system as defined in claim 13 wherein the image processing apparatus further comprises movement controlling means for controlling operations of the object moving section.

17. An imaging system as defined in claim 13 wherein the casing is a dark box, which blocks out external light, and
the image processing apparatus further comprises movement controlling means for controlling operations of the object moving section.

18. An imaging system as defined in claim 13 wherein the excitation light source comprises a downward irradiating excitation light source, which is secured to an upper side of the object support section, and the downward irradiating excitation light source is provided with an excitation light producing section, which produces the excitation light and is located on the side outward from the casing, and an excitation light guiding section for guiding the excitation light, which has been produced by the excitation light producing section, to the region within the casing.

19. An imaging system as defined in claim 13 wherein the object moving section comprises a motor, a shaft connected to the motor, pulleys secured to the shaft, and pulley belts, each of which is threaded over one of the pulleys and is secured to the object support section.

20. An imaging system as defined in claim 13 wherein the correcting condition setting means is capable of accessing a correction table, the correction table storing information representing the correcting conditions, which have been set previously with respect to each of regions of the object support section in accordance with the distribution of illuminances of the excitation light, which distribution is formed on the object support section by the excitation light source, and the correcting condition setting means extracts the correcting conditions with respect to the imaging region from the correction table and sets the thus extracted correcting conditions.

* * * * *